United States Patent
Rudnic et al.

(10) Patent No.: US 7,074,417 B2
(45) Date of Patent: Jul. 11, 2006

(54) MULTIPLE-DELAYED RELEASE ANTI-VIRAL PRODUCT, USE AND FORMULATION THEREOF

(75) Inventors: Edward M. Rudnic, N. Potomac, MD (US); James D. Isbister, Potomac, MD (US); Donald J. Treacy, Jr., Annapolis, MD (US); Sandra E. Wassink, Frederick, MD (US)

(73) Assignee: Advancis Pharmaceutical Corporation, Germantown, MD (US)

( * ) Notice: Subject to any disclaimer, the term of this patent is extended or adjusted under 35 U.S.C. 154(b) by 0 days.

(21) Appl. No.: 10/211,729

(22) Filed: Aug. 2, 2002

(65) Prior Publication Data

US 2003/0104056 A1 Jun. 5, 2003

Related U.S. Application Data

(63) Continuation-in-part of application No. 09/791,906, filed on Feb. 22, 2001, now Pat. No. 6,541,014.

(51) Int. Cl.
*A61K 9/00* (2006.01)
*A61K 9/48* (2006.01)
*A61K 9/20* (2006.01)
*A61K 9/14* (2006.01)
*A61K 9/16* (2006.01)

(52) U.S. Cl. ............ 424/400; 424/451; 424/464; 424/489; 424/490; 424/492; 424/497; 424/502

(58) Field of Classification Search ........ 424/400, 424/451, 464, 489, 490, 492, 497, 502
See application file for complete search history.

(56) References Cited

U.S. PATENT DOCUMENTS

| | | | | |
|---|---|---|---|---|
| 4,435,173 A | 3/1984 | Siposs et al. | ......... | 609/155 |
| 4,616,008 A | 10/1986 | Hirai et al. | ......... | 514/200 |
| 4,794,001 A | 12/1988 | Mehta et al. | ......... | 424/458 |
| 4,831,025 A | 5/1989 | Godtfredsen et al. | ......... | 514/195 |
| 4,904,476 A | 2/1990 | Mehta et al. | ......... | 424/456 |
| 4,915,953 A | 4/1990 | Jordan et al. | ......... | 424/473 |
| 4,971,805 A | 11/1990 | Kitanishi et al. | ......... | 424/494 |
| 5,011,692 A | 4/1991 | Fujioka et al. | ......... | 424/426 |
| 5,110,597 A | 5/1992 | Wong et al. | ......... | 424/438 |
| 5,213,808 A | 5/1993 | Bar-Shalom et al. | ......... | 424/273 |
| 5,229,131 A | 7/1993 | Amidon et al. | ......... | 424/451 |
| 5,395,626 A | 3/1995 | Kotwal et al. | ......... | 424/472 |
| 5,401,512 A | 3/1995 | Rhodes et al. | ......... | 424/458 |
| 5,414,014 A | 5/1995 | Schneider et al. | ......... | 514/535 |
| 5,445,829 A | 8/1995 | Paradissis et al. | ......... | 424/480 |
| 5,462,747 A | 10/1995 | Radebaugh et al. | ......... | 424/465 |
| 5,472,708 A | 12/1995 | Chen | ......... | 424/451 |
| 5,508,040 A | 4/1996 | Chen | ......... | 424/451 |
| 5,567,441 A | 10/1996 | Chen | ......... | 424/494 |
| 5,672,359 A | 9/1997 | Digenis et al. | ......... | 424/463 |
| 5,719,132 A | 2/1998 | Lin et al. | ......... | 514/50 |
| 5,827,531 A | 10/1998 | Morrison et al. | ......... | 424/450 |
| 5,840,329 A * | 11/1998 | Bai | | |
| 5,877,243 A | 3/1999 | Sarangapani | ......... | 524/139 |
| 5,910,322 A | 6/1999 | Rivett et al. | ......... | 424/484 |
| 6,027,748 A | 2/2000 | Conte et al. | ......... | 424/458 |
| 6,132,771 A | 10/2000 | Depui et al. | ......... | 424/468 |
| 6,294,199 B1 | 9/2001 | Conley et al. | ......... | 424/468 |
| 6,358,525 B1 * | 3/2002 | Guo et al. | | |
| 2001/0046984 A1 | 11/2001 | Rudnic et al. | ......... | 514/210.09 |
| 2001/0048944 A1 | 12/2001 | Rudnic et al. | ......... | 424/468 |
| 2002/0004070 A1 | 1/2002 | Rudnic et al. | ......... | 424/468 |
| 2002/0004499 A1 | 1/2002 | Rudnic et al. | ......... | 514/192 |

FOREIGN PATENT DOCUMENTS

| | | |
|---|---|---|
| WO | 94/27557 | 12/1994 |
| WO | 95/20946 | 8/1995 |
| WO | 96/04908 | 2/1996 |
| WO | 98/22091 | 5/1998 |

* cited by examiner

*Primary Examiner*—Humera N. Sheikh
(74) *Attorney, Agent, or Firm*—Elliot M. Olstein; Raymond E. Stauffer

(57) ABSTRACT

An anti-viral product is comprised of at least three delayed release dosage forms, each of which has a different release profile, with the $C_{max}$ for the anti-viral product being reached in less than about twelve hours after initial release of anti-viral from the product.

33 Claims, No Drawings

MULTIPLE-DELAYED RELEASE ANTI-VIRAL PRODUCT, USE AND FORMULATION THEREOF

This application is a continuation-in-part of U.S. application Ser. No. 09/791,906, filed on Feb. 22, 2001, now U.S. Pat. No. 6,541,014 which is a continuation-in-part of U.S. application Ser. No. 09/687,237, filed on Oct. 13, 2000, now abandoned.

This invention relates to an anti-viral product, as well as the use and formulation thereof.

A wide variety of anti-virals have been used, and will be used, in order to combat bacterial infection. In general, such anti-virals can be administered by a repeated dosing of immediate release dosage forms, which results in poor compliance or as a controlled release formulation (slow release) at higher administered doses. The present invention is directed to providing for an improved anti-viral product.

In accordance with one aspect of the present invention, there is provided an anti-viral pharmaceutical product which is comprised of at least two, preferably at least three, anti-viral dosage forms. Such dosage forms are formulated so that each of the dosage forms has a different release profile.

In a particularly preferred embodiment, there are at least two, preferably at least three dosage forms, each of which has a different release profile and the release profile of each of the dosage forms is such that the dosage forms each start release of the anti-viral contained therein at different times after administration of the anti-viral product.

Thus, in accordance with an aspect of the present invention, there is provided a single or unitary anti-viral product that has contained therein at least two, preferably at least three anti-viral dosage forms, each of which has a different release profile, whereby the anti-viral contained in each of such dosage forms is released at different times.

In accordance with a further aspect of the invention, the anti-viral product may be comprised of at least four different dosage forms, each of which starts to release the anti-viral contained therein at different times after administration of the anti-viral product.

The anti-viral product generally does not include more than five dosage forms with different release times.

In accordance with a preferred embodiment, the anti-viral product has an overall release profile such that when administered the maximum serum concentration of the total anti-viral released from the product is reached in less than twelve hours, preferably in less than eleven hours in each case after initial release of the anti-viral. In an embodiment, the maximum serum concentration of the total anti-viral released from the anti-viral product is achieved no earlier than four hours after initial release of the anti-viral.

In accordance with one preferred embodiment of the invention, there are at least three dosage forms, each of which is a delayed release dosage form (which may be a pH sensitive or a non-pH sensitive delayed dosage form, depending on the type of anti-viral product). More particularly, the anti-viral release from the second of the at least three dosage forms achieves a $C_{max}$ (maximum serum concentration in the serum) at a time after the anti-viral released from the first of the at least three dosage forms achieves a $C_{max}$ in the serum, and the anti-viral released from the third dosage form achieves a $C_{max}$ in the serum after the $C_{max}$ of anti-viral released from the second dosage form. As used herein first, second, third, etc., refers to the order in which anti-viral is released from the dosage form.

In one embodiment, the second of the at least two dosage forms initiates release of the anti-viral contained therein at least one hour after the first dosage form initiates release, with the initiation of the release therefrom generally occurring no more than six hours after initiation of release of anti-viral from the first dosage form of the at least three dosage forms.

In general, the first dosage form produces a $C_{max}$ for the anti-viral released therefrom within from about 0.5 to about 2 hours after initiation of release, with the second dosage form of the at least three dosage forms producing a $C_{max}$ for the anti-viral released therefrom in no more than about four hours after initiation of release from the first dosage form. Thus, $C_{max}$ for the second dosage form is achieved after $C_{max}$ for the first dosage form and generally in no more than about 2 to about 3.5 hours after $C_{max}$ is achieved from the first dosage form. In general, the $C_{max}$ for such second dosage form is achieved no earlier than two hours after initiation of release from the first dosage form; however, it is possible within the scope of the invention to achieve $C_{max}$ in a shorter period of time.

As hereinabove indicated, the anti-viral product may contain at least three or at least four or more different dosage forms. For example, if the anti-viral product includes a third dosage form, the anti-viral released therefrom reaches a $C_{max}$ at a time later than the $C_{max}$ is achieved for the anti-viral released from each of the first and second dosage forms. In a preferred embodiment, release of anti-viral from the third dosage form is started after initiation of release of anti-viral from both the first dosage form and the second dosage form. In one embodiment, $C_{max}$ for anti-viral release from the third dosage form is achieved within eight hours after initiation of release from the first dosage form.

In general, the first dosage form initiates release of anti-viral at a time later than anti-viral would be released from an immediate release dosage form. For example, the first dosage form would initiate release within 1 to four hours after administration of the product.

In another embodiment, the anti-viral product contains at least four delayed release dosage forms, with each of the at least four dosage forms having different release profiles, whereby the anti-viral release from each of the at least four different dosage forms achieves a $C_{max}$ at a different time.

As hereinabove indicated, in a preferred embodiment, irrespective of whether the anti-viral contains at least two or at least three or at least four different delayed release dosage forms each with a different release profile, $C_{max}$ for all the anti-viral released from the anti-viral product is achieved in less than twelve hours after release is initiated from the first dosage form., and more generally is achieved in less than eleven hours.

In a preferred embodiment, the anti-viral product is a once a day product, whereby after administration of the anti-viral product, no further product is administered during the day; i.e., the preferred regimen is that the product is administered only once over a twenty-four hour period. Thus, in accordance with the present invention, there is a single administration of an anti-viral product with the anti-viral being released in a manner such that overall anti-viral release is effected with different release profiles in a manner such that the overall $C_{max}$ for the anti-viral product is reached in less than twelve hours after first release of anti-viral. The term single administration means that the total anti-viral administered over a twenty-four hour period is administered at the same time, which can be a single tablet or capsule or two or more thereof, provided that they are administered at essentially the same time.

Applicant has found that a single dosage anti-viral product comprised of at least three anti-viral dosage forms each having a different release profile is an improvement over a single dosage anti-viral product comprised of an anti-viral dosage form having a single release profile. Each of the dosage forms of anti-viral in a pharmaceutically acceptable carrier may have one or more anti-virals and each of the dosage forms may have the same anti-viral or different anti-virals.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of anti-viral may occur. Such "leakage" is not "release" as used herein.

If at least four dosage forms are used, the fourth of the at least four dosage form may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, anti-viral release from such fourth dosage form may be initiated prior to or after release from the second or third dosage form.

The anti-viral product of the present invention, as hereinabove described, may be formulated for administration by a variety of routes of administration. For example, the anti-viral product may be formulated in a way that is suitable for topical administration; administration in the eye or the ear; rectal or vaginal administration; as nose drops; by inhalation; as an injectable; or for oral administration. In a preferred embodiment, the anti-viral product is formulated in a manner such that it is suitable for oral administration.

For example, in formulating the anti-viral product for topical administration, such as by application to the skin, the at least two different dosage forms, each of which contains an anti-viral, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide an anti-viral product in the form of a patch, which includes anti-viral dosage forms having different release profiles, as hereinabove described.

In addition, the anti-viral product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the anti-viral product with at least three different dosage forms with different release profiles may be formulated for rectal or vaginal administration, as known in the art. This may take the form of a cream or emulsion, or other dissolvable dosage form similar to those used for topical administration.

As a further embodiment, the anti-viral product may be formulated for use in inhalation therapy by coating the particles and micronizing the particles for inhalation.

In a preferred embodiment, the anti-viral product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary anti-viral product. Thus, for example, anti-viral products may include a first dosage form in the form of a tablet that is an immediate release tablet, and may also include two or more additional tablets, each of which provides for a delayed release of the anti-viral, as hereinabove described, whereby the $C_{max}$ of the anti-viral released from each of the tablets is reached at different times, with the $C_{max}$ of the total anti-viral released from the anti-viral product being achieved in less than twelve hours after anti-viral is first released.

The formulation of an anti-viral product including at least three dosage forms with different release profiles for different routes of administration is deemed to be within the skill of the art from the teachings herein. As known in the art, with respect to delayed release, the time of release can be controlled by the concentration of anti-virals in the coating and/or the thickness of the coating.

In formulating an anti-viral product in accordance with the invention, in one embodiment, the first dosage form of the product generally provides from about 20% to about 50% of the total dosage of anti-viral to be delivered by the product, with such first dosage form generally providing at least 25% of the total dosage of the anti-viral to be delivered by the product. In many cases, the first dosage form provides from about 20% to about 30% of the total dosage of anti-viral to be delivered by the product; however, in some cases it may be desirable to have the first dosage form provide for about 45% to about 50% of the total dosage of anti-viral to be delivered by the product.

The remaining dosage forms deliver the remainder of the anti-viral. In one embodiment, each of the delayed release dosage forms after the first delayed release dosage form may provide about equal amounts of anti-viral; however, they may also be formulated so as to provide different amounts.

In accordance with the present invention, each of the dosage forms contains the same anti-viral; however, each of the dosage forms may contain more than one anti-viral.

In one embodiment, where the composition contains three delayed release components, the first component provides from 20% to 35% (preferably 20% to 30%), by weight, of the total anti-viral; where there is four delayed release components, the first delayed release component provides from 15% to 30%, by weight, of the total anti-viral; and where there are five delayed release components, the first delayed release component provides from 10% to 25%, by weight, of the total anti-viral.

With respect to the delayed release components, where there are three delayed release components, the second delayed release component provides from 30% to 60%, by weight, of the total anti-viral provided by the second and third delayed release components with the third delayed release component providing the remainder of the anti-viral.

Where there are four delayed release components, the second released component provides 20% to 35% by weight of the total anti-viral provided by the second, third and fourth delayed release components, the next in time delayed release component provides from 20% to 40%, by weight, of the anti-viral provided by the second, third and fourth delayed release components and the last in time providing the remainder of the anti-viral provided by the second, third and fourth delayed release components.

When there are five delayed release components, the second delayed release component provides from 15% to 30%, by weight, the next in time delayed release component provides from 15% to 30%, the next in time delayed release component provides from 20% to 35%, by weight, and the last in time delayed release component provides from 20% to 35%, by weight, in each case of the total anti-viral provided by the second, third, fourth and fifth delayed release components.

An Immediate Release Component

The immediate release portion of this system can be a mixture of ingredients that breaks down quickly after administration to release the anti-viral. This can take the form of either a discrete pellet or granule that is mixed in with, or compressed with, the other three components.

The materials to be added to the anti-virals for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000–10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05–15% (W/W).

The Non-pH Sensitive Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5–25% (W/W) of this component.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4–20% (W/W).

Sustained Release Component

The components in this composition are the same as the immediate release component, but with additional polymers integrated into the composition, or as coatings over the pellet or granule.

The kind of materials useful for this purpose can be, but are not limited to, ethylcellulose, hydroxypropylmethylcellulose, hydroxypropylcellulose, hydroxyethylcellulose, carboxymethylcellulose, methylcellulose, nitrocellulose, Eudragit R, and Eudragit RL, Carbopol, or polyethylene glycols with molecular weights in excess of 8,000 daltons.

These materials can be present in concentrations from 4–20% (W/W).

As hereinabove indicated, the units comprising the anti-viral composition of the present invention can be in the form of discrete pellets or particles contained in the capsule, or particles embedded in a tablet or suspended in a liquid suspension.

The anti-viral composition of the present invention may be administered, for example, by any of the following routes of administration: sublingual, transmucosal, transdermal, parenteral, etc., and preferably is administered orally. The composition includes a therapeutically effective amount of the anti-viral, which amount will vary with the anti-viral to be used, the disease or infection to be treated, and the number of times that the composition is to be delivered in a day. The composition is administered to a host in an amount effective for treating a bacterial infection.

The following are representative examples of some antivirals that may be used in the product of the invention: Acyclovir, Amantadine, Amprenavir, Cidofovir, Delavirdine, Didanosine, Famciclovir, Foscarnet, Ganciclovir, Indinavir, Interferon, Lamivudine, Nelfinavir, Nevirapine, Palivizumab, Penciclovir, Ribavirin, Rimantadine, Ritonavir, Saquinavir, Stavudine, Trifluridine, Valacyclovir, Vidarabine, Zalcitabine, Zidovudine The invention will be further described with respect to the following examples; however, the scope of the invention is not limited thereby. All percentages in this specification, unless otherwise specified, are by weight.

ANTIVIRAL EXAMPLES

Non-pH Sensitive Delayed Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| | Ingredient | Conc. (% W/W) |
|---|---|---|
| Example 1: | Fluorouracil | 65% (W/W) |
| | Microcrystalline cellulose | 20 |
| | Polyox | 7.5 |
| | Croscarmellose sodium | 7.5 |
| Example 2: | Fluorouracil | 55% (W/W) |
| | Microcrystalline cellulose | 25 |
| | Polyox | 10 |
| | Glyceryl monooleate | 10 |
| Example 3: | Fluorouracil | 75% (W/W) |
| | Polyox | 10 |
| | Hydroxypropylcellulose | 5 |
| | Croscarmellose sodium | 10 |
| Example 4: | Dexamethasone | 65% (W/W) |
| | Microcrystalline cellulose | 20 |
| | Polyox | 7.5 |
| | Croscarmellose sodium | 7.5 |
| Example 5: | Dexamethasone | 55% (W/W) |
| | Microcrystalline cellulose | 25 |
| | Polyox | 10 |
| | Glyceryl monooleate | 10 |
| Example 6: | Dexamethasone | 75% (W/W) |
| | Polyox | 10 |
| | Hydroxypropylcellulose | 5 |
| | Croscarmellose sodium | 10 |
| Example 7: | Valrubicin | 65% (W/W) |
| | Microcrystalline cellulose | 20 |
| | Polyox | 7.5 |
| | Croscarmellose sodium | 7.5 |
| Example 8: | Valrubicin | 55% (W/W) |
| | Microcrystalline cellulose | 25 |
| | Polyox | 10 |
| | Glyceryl monooleate | 10 |
| Example 9: | Valrubicin | 75% (W/W) |
| | Polyox | 10 |
| | Hydroxypropylcellulose | 5 |
| | Croscarmellose sodium | 10 |
| Example 10: | Tretinoin | 65% (W/W) |
| | Microcrystalline cellulose | 20 |
| | Polyox | 7.5 |
| | Croscarmellose sodium | 7.5 |
| Example 11: | Tretinoin | 55% (W/W) |
| | Microcrystalline cellulose | 25 |
| | Polyox | 10 |
| | Glyceryl monooleate | 10 |
| Example 12: | Tretinoin | 75% (W/W) |
| | Polyox | 10 |
| | Hydroxypropylcellulose | 5 |
| | Croscarmellose sodium | 10 |

Enteric Release Component

Formulate the ingredients by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| | Ingredient | Conc. (% W/W) |
|---|---|---|
| Example 13: | Acyclovir | 65% (W/W) |
| | Microcrystalline cellulose | 20 |
| | Cellulose Acetate Pthalate | 15 |
| Example 14: | Acyclovir | 55% (W/W) |
| | Microcrystalline cellulose | 25 |
| | Cellulose Acetate Pthalate | 10 |
| | Hydroxypropylmethylcellulose | 10 |
| Example 15: | Acyclovir | 65% (W/W) |
| | Polyox | 20 |
| | Hydroxypropylcellulose pthalate | 10 |
| | Eudragit L 30D | 5 |
| Example 16: | Valacyclovir | 80% (W/W) |
| | Lactose | 10 |
| | Eudragit L 30D | 10 |
| Example 17: | Valacyclovir | 70% (W/W) |
| | Polyethylene glycol 4000 | 20 |
| | Cellulose acetate pthalate | 10 |
| Example 18: | Ribavirin | 60% (W/W) |
| | Polyethylene glycol 2000 | 10 |
| | Lactose | 20 |
| | Eudragit L 30D | 10 |
| Example 19: | Ribavirin | 70% (W/W) |
| | Microcrystalline cellulose | 20 |
| | Cellulose acetate pthalate | 10 |

Sustained Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| | Ingredient | Conc. (% W/W) |
|---|---|---|
| Example 20: | Acyclovir | 65% (W/W) |
| | Ethylcellulose | 20 |
| | Polyox | 10 |
| | Hydroxypropylmethylcellulose | 5 |
| Example 21: | Acyclovir | 55% (W/W) |
| | Lactose | 25 |
| | Polyox | 10 |
| | Glyceryl monooleate | 10 |
| Example 22: | Acyclovir | 70% (W/W) |
| | Polyox | 20 |
| | Hydroxypropylcellulose | 10 |
| Example 23: | Zidovudine | 75% (W/W) |
| | Lactose | 15 |
| | Hydroxypropylcellulose | 5 |
| | Ethylcellulose | 5 |
| Example 24: | Zidovudine | 75% (W/W) |
| | Polyethylene glycol 4000 | 10 |
| | Lactose | 10 |
| | Eudragit RL 30D | 5 |
| Example 25: | Zidovudine | 80% (W/W) |
| | Polyethylene glycol 8000 | 10 |
| | Hydroxypropylmethylcellulose | 5 |
| | Eudgragit RS 30D | 5 |
| Example 26: | Valacyclovir | 75% (W/W) |
| | Hydroxyethylcellulose | 10 |
| | Polyethylene glycol 4000 | 10 |
| | Hydroxypropylcellulose | 5 |
| Example 27: | Valacyclovir | 75% (W/W) |
| | Lactose | 10 |
| | Povidone (PVP) | 10 |
| | Polyethylene glycol 2000 | 5 |
| Example 28: | Ribavirin | 75% (W/W) |
| | Polyethylene glycol 4000 | 10 |
| | Povidone (PVP) | 10 |
| | Hydroxypropylcellulose | 5 |
| Example 29: | Ribavirin | 75% (W/W) |
| | Lactose | 15 |
| | Polyethylene glycol 4000 | 5 |
| | Polyvinylpyrrolidone | 5 |

-continued

| | Ingredient | Conc. (% W/W) | |
|---|---|---|---|
| Example 30: | Zidovudine | 40% | (W/W) |
| | Eudragit S100 | 50 | |
| | Triethyl Citrate | 10 | |
| Example 31: | Zidovudine | 50% | (W/W) |
| | Sureteric | 50 | |
| Example 32: | Zidovudine | 50% | (W/W) |
| | Eudragit S100 | 45 | |
| | Triethyl Citrate | 5 | |

All Delayed Release Three Pulses

Example 33

Antiviral Pellet Formulation and Preparation Procedure

Pellet Formulations

The composition of the Antiviral pellets provided in Table 1.

TABLE 1

Composition of Antiviral Pellets

| Component | Percentage (%) |
|---|---|
| Antiviral drug | 92 |
| Avicel PH 101 | 6.0 |
| Polyoxyl 35 Castor Oil* | 1.0 |
| Hydroxypropyl methylcellulose, NF* | 1.0 |
| Purified Water | ** |
| Total | 100 |

*Hydroxypropyl methylcellulose and Cremaphor EL were added as a 2.9% w/w aqueous solution during wet massing.
**Removed during processing Preparation Procedure for Antiviral Pellets
- Blend Antiviral and Avicel® PH 101 using a high shear mixer.
- Add the hydroxypropyl methylcellulose and Polyoxyl 35 Castor Oil binder solution slowly into the powder blend under continuous mixing.
- Extrude the wet mass using an LCI Bench Top Granulator. The diameter of the screen of the Bench Top Granulator is 0.8 mm.
- Spheronize the extrudate using a QJ-230 Spheronizer using a small cross section plate.
- Dry the spheronized pellets at 60° C. using a fluid bed dryer until the exhaust temperature reaches 40° C.
- Pellets between 20 and 40 Mesh were collected for further processing.

Antiviral Pulse One Pellet Formulation and Preparation Procedure

Preparation of an AQOAT AS-LF Aqueous Coating Dispersion

Dispersion Formulation

The composition of the aqueous AQOAT AS-LF aqueous coating dispersion applied to the Antiviral pellets is provided below in Table 2.

TABLE 2

AQOAT AS-LF Aqueous Coating Dispersion

| Component | Percentage (%) |
|---|---|
| AQOAT AS-LF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-LF Aqueous Dispersion
- Add triethyl citrate (TEC) to the purified water with stirring.
- Add the sodium lauryl sulfate (SLS) to the TEC dispersion with stirring and completely until completely dissolved.
- Add the AQOAT to the TEC/SLS dispersion and stir for at least 30 minutes.
- Add the talc to the AQOAT dispersion and until completely mixed and for at least 30 minutes.
- Screen the dispersion through a No. 60 mesh sieve prior to coating.
- Continue to stir the dispersion until the coating process is complete.

Coating Conditions for the Application of AQOAT AS-LF Aqueous Coating Dispersion The following coating parameters were used for coating of the AQOAT AS-LF film coating dispersion.

| | |
|---|---|
| Coating Equipment | STREA 1 ™ |
| | Table Top Laboratory Fluid Bed Coater |
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Antiviral pellets with AQOAT AS-LF film coating dispersion such that you apply 30% coat weight gain to the pellets.

Antiviral Pulse Two Pellet Formulation and Preparation Procedure

Preparation of an AQOAT AS-HF Aqueous Coating Dispersion

Dispersion Formulation

The composition of the aqueous AQOAT AS-HF aqueous coating dispersion applied to the Antiviral pellets is provided below in Table 3.

TABLE 3

AQOAT AS-HF Aqueous Coating Dispersion

| Component | Percentage (%) |
|---|---|
| AQOAT AS-HF | 7.0 |
| Triethyl Citrate | 2.0 |
| Talc | 2.1 |

TABLE 3-continued

AQOAT AS-HF Aqueous Coating Dispersion

| Component | Percentage (%) |
|---|---|
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-HF Aqueous Dispersion

- Add triethyl citrate (TEC) to the purified water with stirring.
- Add the sodium lauryl sulfate (SLS) to the TEC dispersion with stirring and completely until completely dissolved.
- Add the AQOAT to the TEC/SLS dispersion and stir for at least 30 minutes.
- Add the talc to the AQOAT dispersion and until completely mixed and for at least 30 minutes.
- Screen the dispersion through a No. 60 mesh sieve prior to coating.
- Continue to stir the dispersion until the coating process is complete.

Coating Conditions for the Application of AQOAT AS-HF Aqueous Coating Dispersion The following coating parameters were used for coating of the AQOAT AS-HF film coating dispersion.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Antiviral pellets with AQOAT AS-HF film coating dispersion such that you apply 30% coat weight gain to the pellets.

Antiviral Pulse Three Pellet Formulation and Preparation Procedure

Preparation of an Eudragit® FS 30D Aqueous Coating Dispersion

Dispersion Formulation

The composition of the aqueous Eudragit® FS 30D dispersion applied to the Antiviral pellets is provided below in Table 4.

TABLE 4

Eudragit ® FS 30D Aqueous Coating Dispersion

| Component | Percentage (%) |
|---|---|
| Eudragit ® FS 30D | 54.8 |
| Triethyl Citrate | 0.9 |
| Talc | 3.3 |
| Purified Water* | 41.0 |

TABLE 4-continued

Eudragit ® FS 30D Aqueous Coating Dispersion

| Component | Percentage (%) |
|---|---|
| Solid Content | 20.6 |
| Polymer Content | 16.4 |

*Removed during processing

Preparation Procedure for an Eudragit® FS 30D Aqueous Dispersion

- Disperse triethyl citrate (TEC) in the purified water.
- Add the talc in the triethyl citrate dispersion.
- Homogenize the dispersion using a homogenizer.
- Add slowly the Eudragit® FS 30D dispersion to the talc/TEC dispersion with stirring.
- Continue to stir the coating dispersion until the coating process is complete.

Coating Conditions for the Application of Eudragit FS30D Aqueous Coating Dispersion The following coating parameters were used for coating with each of the Eudragit® FS 30 D aqueous film coating.

| | |
|---|---|
| Coating Equipment | STREA 1 ™ Table Top Laboratory Fluid Bed Coater |
| Spray nozzle diameter | 1.2 mm |
| Material Charge | 300 gram |
| Inlet Air Temperature | 38° C. |
| Outlet Air Temperature | 22° C. |
| Atomization Air Pressure | 1.6 Bar |
| Pump Rate | 6 gram per minute |

Coat pellets with Eudragit FS 30D coating dispersion dispersion such that you apply 30% coat weight gain to the pellets.

Antiviral Tablets

Tableting of the Antiviral Pellets

TABLE 5

Composition of Antiviral Tablets

| Component | Percentage (%) |
|---|---|
| Silicified microcrystalline cellulose | 21.6 |
| Lactose monohydrate | 13.0 |
| Povidone | 5.0 |
| Pulse One Pellets | 18.3 |
| Pulse Two Pellets | 18.3 |
| Pulse Three Pellets | 18.3 |
| Croscarmellose sodium | 5.0 |
| Magnesium stearate | 0.5 |
| Total | 100 |

- Blend the silicified microcrystalline cellulose, lactose monohydrate, povidone, colloidal silicon dioxide and Antiviral coated pellets for 15 minutes in a tumble blender.
- Add the magnesium stearate to the blender, and blend for 5 minutes.
- Compress the blend on a rotary tablet press.
- The fill weight should be adjusted to achieve the desired dose.

Encapsulation of the Antiviral Pellets

Pellets are filled into hard gelatin capsules at a ratio of 33.4%: 33.3%: 33.3%: Pulse One, Pulse Two, and Pulse Three Pellets respectively. The capsule is filled with the three different pellets to achieve the desired dose.

The present invention is particularly advantageous in that there is provided an antiviral product which provides an improvement over twice a day administration of the antiviral and an improvement over a once a day administration of the antiviral.

Numerous modification and variations of the present invention are possible in light of the above teachings and therefore, within the scope of the appended claims the invention may be practiced otherwise than as particularly described.

All Delayed Release Four Pulses

Example 34

Antiviral Pellet Formulation and Preparation Procedure

Pellet Formulations

The composition of the Antiviral pellets provided in Table 6.

TABLE 6

Composition of Antiviral Pellets

| Component | Percentage (%) |
|---|---|
| Antiviral drug | 92 |
| Avicel PH 101 | 6.0 |
| Polyoxyl 35 Castor Oil* | 1.0 |
| Hydroxypropyl methylcellulose, NF* | 1.0 |
| Purified Water | ** |
| Total | 100 |

*Hydroxypropyl methylcellulose and Cremaphor EL were added as a 2.9% w/w aqueous solution during wet massing.
**Removed during processing Preparation Procedure for Antiviral Pellets Blend Antiviral and Avicel® PH 101 using a high shear mixer.

Add the hydroxypropyl methylcellulose and Polyoxyl 35 Castor Oil binder solution slowly into the powder blend under continuous mixing.

Extrude the wet mass using an LCI Bench Top Granulator. The diameter of the screen of the Bench Top Granulator is 0.8 mm.

Spheronize the extrudate using a QJ-230 Spheronizer using a small cross section plate.

Dry the spheronized pellets at 60° C. using a fluid bed dryer until the exhaust temperature reaches 40° C.

Pellets between 20 and 40 Mesh were collected for further processing.

Antiviral Pulse One Pellet Formulation and Preparation Procedure

Preparation of an AQOAT AS-LF Aqueous Coating Dispersion

Dispersion Formulation

The composition of the aqueous AQOAT AS-LF aqueous coating dispersion applied to the Antiviral pellets is provided below in Table 7.

TABLE 7

AQOAT AS-LF Aqueous Coating Dispersion

| Component | Percentage (%) |
|---|---|
| AQOAT AS-LF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-LF Aqueous Dispersion

Add triethyl citrate (TEC) to the purified water with stirring.

Add the sodium lauryl sulfate (SLS) to the TEC dispersion with stirring and completely until completely dissolved.

Add the AQOAT to the TEC/SLS dispersion and stir for at least 30 minutes.

Add the talc to the AQOAT dispersion and until completely mixed and for at least 30 minutes.

Screen the dispersion through a No. 60 mesh sieve prior to coating.

Continue to stir the dispersion until the coating process is complete.

Coating Conditions for the Application of AQOAT AS-LF Aqueous Coating Dispersion The following coating parameters were used for coating of the AQOAT AS-LF film coating dispersion.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Antiviral pellets with AQOAT AS-LF film coating dispersion such that you apply 30% coat weight gain to the pellets.

Antiviral Pulse Two Pellet Formulation and Preparation Procedure

Preparation of an Eudragit® L 30 D-55 Aqueous Coating Dispersion

Dispersion Formulation

The composition of the aqueous Eudragit L30D-55 aqueous coating dispersion applied to the Antiviral pellets is provided below in Table 8.

TABLE 8

Eudragit ® L 30 D-55 Aqueous Coating Dispersion

| Component | Percentage (%) |
|---|---|
| Eudragit ® L 30D-55 | 44.4 |
| Triethyl Citrate | 1.3 |
| Talc | 6.7 |

TABLE 8-continued

Eudragit® L 30 D-55 Aqueous Coating Dispersion

| Component | Percentage (%) |
|---|---|
| Purified Water* | 47.6 |
| Solid Content | 21.3 |
| Polymer Content | 13.3 |

*Removed during processing

Preparation Procedure for an Eudragit® L 30D-55 Aqueous Dispersion

Disperse triethyl citrate (TEC) in the purified water.

Add the talc into the triethyl citrate dispersion.

Homogenize the dispersion using a homogenizer.

Add the TEC/talc dispersion to Eudragit L30D-55 latex dispersion and stir for at least 30 minutes.

Screen the dispersion through a No. 60 mesh sieve prior to coating.

Continue to stir the dispersion until the coating process is complete.

Coating Conditions for the Application of Eudragit L30D-55 Aqueous Coating Dispersion The following coating parameters were used for coating of the Eudragit® L 30 D-55 film coating dispersion.

| | |
|---|---|
| Coating Equipment | STREA 1 ™ |
| | Table Top Laboratory Fluid Bed Coater |
| Spray nozzle diameter | 1.0 mm |
| Material Charge | 300 gram |
| Inlet Air Temperature | 45° C. |
| Outlet Air Temperature | 32 to 35° C. |
| Atomization Air Pressure | 1.6 Bar |
| Pump Rate | 3–4 gram per minute |

Coat Antiviral pellets with Eudragit L30 D-55 film coating dispersion such that you apply 30% coat weight gain to the pellets.

Antiviral Pulse Three Pellets Formulation and Preparation Procedure

Preparation of an AQOAT AS-HF Aqueous Coating Dispersion

Dispersion Formulation

The composition of the aqueous AQOAT AS-HF aqueous coating dispersion applied to the Antiviral pellets is provided below in Table 9.

TABLE 9

AQOAT AS-HF Aqueous Coating Dispersion

| Component | Percentage (%) |
|---|---|
| AQOAT AS-HF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-HF Aqueous Dispersion

Add triethyl citrate (TEC) to the purified water with stirring.

Add the sodium lauryl sulfate (SLS) to the TEC dispersion with stirring and completely until completely dissolved.

Add the AQOAT to the TEC/SLS dispersion and stir for at least 30 minutes.

Add the talc to the AQOAT dispersion and until completely mixed and for at least 30 minutes.

Screen the dispersion through a No. 60 mesh sieve prior to coating.

Continue to stir the dispersion until the coating process is complete.

Coating Conditions for the Application of AQOAT AS-HF Aqueous Coating Dispersion The following coating parameters were used for coating of the AQOAT AS-HF film coating dispersion.

| | |
|---|---|
| Coating Equipment | STREA 1 ™ |
| | Table Top Laboratory Fluid Bed Coater |
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Antiviral pellets with AQOAT AS-HF film coating dispersion such that you apply 30% coat weight gain to the pellets.

Antiviral Pulse Four Pellet Formulation and Preparation Procedure

Preparation of an Eudragit® FS 30D Aqueous Coating Dispersion

Dispersion Formulation

The composition of the aqueous Eudragit® FS 30D dispersion applied to the Antiviral pellets is provided below in Table 10.

TABLE 10

Eudragit® FS 30D Aqueous Coating Dispersion

| Component | Percentage (%) |
|---|---|
| Eudragit® FS 30D | 54.8 |
| Triethyl Citrate | 0.9 |
| Talc | 3.3 |
| Purified Water* | 41.0 |
| Solid Content | 20.6 |
| Polymer Content | 16.4 |

*Removed during processing

Preparation Procedure for an Eudragit® FS 30D Aqueous Dispersion

Disperse triethyl citrate (TEC) in the purified water.

Add the talc in the triethyl citrate dispersion.

Homogenize the dispersion using a homogenizer.

Add slowly the Eudragit® FS 30D dispersion to the talc/TEC dispersion with stirring.

Continue to stir the coating dispersion until the coating process is complete.

Coating Conditions for the Application of Eudragit FS30D Aqueous Coating Dispersion The following coating parameters were used for coating with each of the Eudragit® FS 30 D aqueous film coating.

| Coating Equipment | STREA 1 ™ Table Top Laboratory Fluid Bed Coater |
|---|---|
| Spray nozzle diameter | 1.2 mm |
| Material Charge | 300 gram |
| Inlet Air Temperature | 38° C. |
| Outlet Air Temperature | 22° C. |
| Atomization Air Pressure | 1.6 Bar |
| Pump Rate | 6 gram per minute |

Coat pellets with Eudragit FS 30D coating dispersion dispersion such that you apply 30% coat weight gain to the pellets.

Antiviral Tablets

Tableting of the Antiviral Pellets

TABLE 11

Composition of Antiviral Tablets

| Component | Percentage (%) |
|---|---|
| Silicified microcrystalline cellulose | 21.5 |
| Lactose monohydrate | 13.0 |
| Povidone | 5.0 |
| Pulse One Pellets | 13.75 |
| Pulse Two Pellets | 13.75 |
| Pulse Three Pellets | 13.75 |
| Pulse Four Pellets | 13.75 |
| Croscarmellose sodium | 5.0 |
| Magnesium stearate | 0.5 |
| Total | 100 |

Blend the silicified microcrystalline cellulose, lactose monohydrate, povidone, colloidal silicon dioxide and Antiviral coated pellets for 15 minutes in a tumble blender.

Add the magnesium stearate to the blender, and blend for 5 minutes.

Compress the blend on a rotary tablet press.

The fill weight should be adjusted to achieve the desired dose.

Encapsulation of the Antiviral Pellets

Pellets are filled into hard gelatin capsules at a ratio of 25%:25%:25%:25% Pulse One, Pulse Two, Pulse Three and Pulse Four Pellets respectively. The capsule is filled with the four different pellets to achieve the desired dose.

The present invention is particularly advantageous in that there is provided an antiviral product which provides an improvement over twice a day administration of the antiviral and an improvement over a once a day administration of the antiviral.

Numerous modification and variations of the present invention are possible in light of the above teachings and therefore, within the scope of the appended claims the invention may be practiced otherwise than as particularly described.

What is claimed is:

1. A once-a-day anti-viral product comprising: first, second, and third anti-viral dosage forms, each of said anti-viral dosage forms comprising at least one anti-viral and a pharmaceutically acceptable carrier, said first, second, and third anti-viral dosage forms being delayed release dosage forms, and wherein each of said first, second, and third anti-viral dosage forms initiates release at different times and Cmax in serum of the total anti-viral released from said anti-viral product is achieved in less than about 12 hours after initial release of anti-viral, and said once-a-day antiviral product contains the total dosage of the at least one anti-viral for a twenty-four hour period, said product being free of an immediate release dosage form.

2. The product of claim 1, wherein the Cmax for the product is reached no earlier than four hours after initial release of anti-viral.

3. The product of claim 1, wherein the anti-viral released from the first dosage form reaches a Cmax in serum within from about 0.5 hours to about 2 hours after initial release of anti-viral.

4. The product of claim 1, wherein the anti-viral released from the second dosage form reaches a Cmax in serum in no more than about 4 hours after initial release of anti-viral.

5. The product of claim 1, wherein the anti-viral released from the third dosage form reaches a Cmax in serum within 8 hours after initial release of anti-viral.

6. The product of claim 1, wherein the first release dosage form contains at least 20% and no more than 50% of the total dosage of anti-viral.

7. The product of claim 1, wherein the product is an oral dosage form.

8. The product of claim 7, wherein the anti-viral released from the second dosage form reaches a Cmax in the serum after Cmax is reached in the serum for the anti-viral released from the first dosage form.

9. The product of claim 8, wherein the anti-viral released from the third dosage form reaches a Cmax in the serum after Cmax is reached in the serum for the anti-viral released from the second dosage form.

10. The product of claim 9, wherein said second dosage form initiates release of said anti-viral before said third dosage form, wherein said second dosage form provides from 30% to 60% by weight of the total anti-viral released by said second and third dosage forms, and wherein said third dosage form provides the remainder of the total anti-viral released by said second and third dosage forms.

11. The product of claim 1 further comprising a fourth anti-viral dosage form, said fourth anti-viral dosage form comprising at least one anti-viral and a pharmaceutically acceptable carrier and wherein said at least one anti-viral released from said fourth anti-viral dosage form reaches a Cmax in the serum after Cmax is achieved in the serum for anti-viral released from each of said first, second, and third dosage forms.

12. The product of claim 11, wherein said fourth anti-viral dosage form is a delayed release dosage form.

13. The product of claim 12, wherein said second dosage form initiates release of said anti-viral before said third dosage form, wherein said third dosage form initiates release of said anti-viral before said fourth dosage form, wherein said second dosage form provides 20% to 35% by weight of the total anti-viral released by said second, third, and fourth dosage forms, wherein said third dosage form provides from 20% to 40% by weight of the total anti-viral released by said second, third, and fourth dosage forms, and wherein said fourth dosage form provides the remainder of the total anti-viral released by said second, third, and fourth dosage forms.

14. The product of claim 11, wherein the anti-viral released from the first dosage form reaches a Cmax in serum within from about 0.5 hours to about 2 hours after initial release of anti-viral.

15. The product of claim 11, wherein the anti-viral released from the second dosage form reaches a Cmax in serum in no more than about 4 hours after initial release of anti-viral.

16. The product of claim 11, wherein the anti-viral released from the third dosage form reaches a Cmax in serum within 8 hours after initial release of anti-viral.

17. A process for treating a viral infection in a host comprising: administering to a host the anti-viral product of claim 1 once-a-day.

18. A process for treating a viral infection in a host comprising: administering to a host the anti-viral product of claim 2 once-a-day.

19. A process for treating a viral infection in a host comprising: administering to a host the anti-viral product of claim 3 once-a-day.

20. A process for treating a viral infection in a host comprising: administering to a host the anti-viral product of claim 4 once-a-day.

21. A process for treating a viral infection in a host comprising: administering to a host the anti-viral product of claim 5 once-a-day.

22. A process for treating a viral infection in a host comprising: administering to a host the anti-viral product of claim 6 once-a-day.

23. A process for treating a viral infection in a host comprising: administering to a host the anti-viral product of claim 7 once-a-day.

24. A process for treating a viral infection in a host comprising: administering to a host the anti-viral product of claim 8 once-a-day.

25. A process for treating a viral infection in a host comprising: administering to a host the anti-viral product of claim 9 once-a-day.

26. A process for treating a viral infection in a host comprising: administering to a host the anti-viral product of claim 10 once-a-day.

27. A process for treating a viral infection in a host comprising: administering to a host the anti-viral product of claim 1 once-a-day.

28. A process for treating a viral infection in a host comprising: administering to a host the anti-viral product of claim 12 once-a-day.

29. A process for treating a viral infection in a host comprising: administering to a host the anti-viral product of claim 13 once-a-day.

30. A process for treating a viral infection in a host comprising: administering to a host the anti-viral product of claim 14 once-a-day.

31. A process for treating a viral infection in a host comprising: administering to a host the anti-viral product of claim 15 once-a-day.

32. A process for treating a viral infection in a host comprising: administering to a host the anti-viral product of claim 16 once-a-day.

33. A process for treating a patient with an anti-viral agent said process for treating comprising: administering to a patient once-a-day an anti-viral product, said product comprising: first, second, and third dosage forms, wherein each of said dosage forms includes at least one anti-viral agent and a pharmaceutically acceptable carrier; said treating including delayed releases of anti-viral agent from each of said first, second, and third dosage forms, said three delayed releases initiating release of anti-viral agent at different times to produce a Cmax in serum of the total anti-viral agent released from said anti-viral product in less than about 12 hours from the initial release of anti-viral agent; and said treating delivers the total dosage of said at least one anti-viral agent for a twenty-four hour period.

\* \* \* \* \*